US008579607B2

(12) United States Patent
Wampler et al.

(10) Patent No.: US 8,579,607 B2
(45) Date of Patent: Nov. 12, 2013

(54) ROTARY BLOOD PUMP WITH OPPOSING SPINDLE MAGNETS, BORE AND DRIVE WINDINGS

(75) Inventors: Richard K. Wampler, Loomis, CA (US); David M. Lancisi, Folsom, CA (US)

(73) Assignee: Thoratec Corporation, Pleasanton, CA (US)

( * ) Notice: Subject to any disclaimer, the term of this patent is extended or adjusted under 35 U.S.C. 154(b) by 754 days.

(21) Appl. No.: 11/950,328

(22) Filed: Dec. 4, 2007

(65) Prior Publication Data

US 2008/0080983 A1 Apr. 3, 2008

Related U.S. Application Data

(62) Division of application No. 10/940,419, filed on Sep. 14, 2004, now Pat. No. 7,431,688.

(60) Provisional application No. 60/504,233, filed on Sep. 18, 2003.

(51) Int. Cl.
*F04D 29/048* (2006.01)
*F04D 29/047* (2006.01)

(52) U.S. Cl.
USPC ............ 417/423.12; 417/423.7; 415/900

(58) Field of Classification Search
USPC ............ 417/423.7, 423.12, 423.1, 423.14; 604/151; 623/3.14; 415/104, 900
See application file for complete search history.

(56) References Cited

U.S. PATENT DOCUMENTS 3,420,184 A * 1/1969 Englesberg et al. ........... 417/420
3,753,623 A * 8/1973 Wutz ........................... 417/423.4
4,082,376 A * 4/1978 Wehde et al. ................. 310/90.5
4,779,614 A 10/1988 Moise
4,806,080 A 2/1989 Mizobuchi et al.
5,049,134 A 9/1991 Golding et al.
5,055,005 A 10/1991 Kletschka
5,106,273 A * 4/1992 Lemarquand et al. ........ 417/354

(Continued)

FOREIGN PATENT DOCUMENTS

EP 810374 A2 12/1997
EP 1481699 A1 12/2004

(Continued)

OTHER PUBLICATIONS

G.H. Jang, et al., "Nonlinear Dynamic Analysis of a Hydrodynamic Journal Bearing Considering the Effect of a Rotating or Stationary Herringbone Groove," *ASME Journal of Tribology*, STLE/ASME Tribology Conference, San Francisco, California, Oct. 22-24, 2001, pp. 297-304.

(Continued)

*Primary Examiner* — Peter J Bertheaud
(74) *Attorney, Agent, or Firm* — Inskeep IP Group, Inc.

(57) ABSTRACT

Various "contactless" bearing mechanisms including hydrodynamic and magnetic bearings are provided for a rotary pump as alternatives to mechanical contact bearings. In one embodiment, a pump apparatus includes a pump housing defining a pumping chamber. The housing has a spindle extending into the pumping chamber. A spindle magnet assembly includes first and second magnets disposed within the spindle. The first and second magnets are arranged proximate each other with their respective magnetic vectors opposing each other. The lack of mechanical contact bearings enables longer life pump operation and less damage to working fluids such as blood.

14 Claims, 5 Drawing Sheets

(56) References Cited

U.S. PATENT DOCUMENTS

| | | | |
|---|---|---|---|
| 5,112,200 A | 5/1992 | Isaacson et al. | |
| 5,195,877 A | 3/1993 | Kletschka | |
| 5,209,650 A | 5/1993 | Lemieux | |
| 5,211,546 A | 5/1993 | Isaacson et al. | |
| 5,324,177 A | 6/1994 | Golding et al. | |
| 5,360,445 A | 11/1994 | Goldowsky | |
| 5,370,509 A | 12/1994 | Golding et al. | |
| 5,385,581 A | 1/1995 | Bramm et al. | |
| 5,451,147 A * | 9/1995 | Sakagami et al. | 417/423.4 |
| 5,470,208 A | 11/1995 | Kletschka | |
| 5,685,700 A | 11/1997 | Izraelev | |
| 5,695,471 A | 12/1997 | Wampler | |
| 5,713,730 A | 2/1998 | Nosé et al. | |
| 5,746,575 A | 5/1998 | Westphal et al. | |
| 5,840,070 A | 11/1998 | Wampler | |
| 5,890,883 A | 4/1999 | Golding | |
| 5,938,412 A | 8/1999 | Izraelev | |
| 5,947,703 A | 9/1999 | Nojiri et al. | |
| 6,071,093 A | 6/2000 | Hart | |
| 6,080,133 A | 6/2000 | Wampler | |
| 6,120,537 A * | 9/2000 | Wampler | 623/3.14 |
| 6,155,969 A | 12/2000 | Schima et al. | |
| 6,176,848 B1 | 1/2001 | Rau et al. | |
| 6,227,797 B1 | 5/2001 | Watterson et al. | |
| 6,227,817 B1 | 5/2001 | Paden | |
| 6,227,820 B1 | 5/2001 | Jarvik | |
| 6,234,772 B1 | 5/2001 | Wampler | |
| 6,234,998 B1 | 5/2001 | Wampler | |
| 6,244,835 B1 | 6/2001 | Antaki et al. | |
| 6,247,892 B1 | 6/2001 | Kazatchkov et al. | |
| 6,250,880 B1 | 6/2001 | Woodard et al. | |
| 6,264,635 B1 | 7/2001 | Wampler et al. | |
| 6,293,901 B1 | 9/2001 | Prem | |
| 6,368,083 B1 | 4/2002 | Wampler | |
| 6,394,769 B1 | 5/2002 | Bearnson et al. | |
| 6,447,266 B2 | 9/2002 | Antaki et al. | |
| 6,595,762 B2 | 7/2003 | Khanwilkar et al. | |
| 6,609,883 B2 | 8/2003 | Woodard et al. | |
| 6,638,011 B2 | 10/2003 | Woodard et al. | |
| 6,641,378 B2 * | 11/2003 | Davis et al. | 417/423.7 |
| 6,688,861 B2 | 2/2004 | Wampler | |
| 7,074,016 B1 * | 7/2006 | Epstein et al. | 417/348 |
| 2001/0031210 A1 | 10/2001 | Antaki et al. | |
| 2004/0236420 A1 * | 11/2004 | Yamane et al. | 623/3.14 |

FOREIGN PATENT DOCUMENTS

| | | | |
|---|---|---|---|
| WO | WO 94/09274 A1 | 4/1994 | |
| WO | WO 95/00185 A1 | 1/1995 | |
| WO | WO 97/37698 A1 | 10/1997 | |
| WO | WO 98/41759 A1 | 9/1998 | |
| WO | WO 98/46879 A1 | 10/1998 | |
| WO | WO 99/01663 A1 | 1/1999 | |
| WO | WO 99/12587 A1 | 3/1999 | |
| WO | WO 99/53974 A2 | 10/1999 | |
| WO | WO 00/32256 | 6/2000 | |
| WO | WO 03006088 A1 * | 1/2003 | A61M 1/10 |

OTHER PUBLICATIONS

G.H. Jang, et al., "Stability Analysis of a Hydrodynamic Journal Bearing with Rotating Herringbone Grooves," *ASME Journal of Tribology*, ASME/STLE Tribology Conference, Cancun, Mexico, Oct. 27-30, 2002, pp. 291-300.

"Fluid Dynamic Bearings (FDB): New Technology to Replace Ball Bearings in Western Digital Hard Drives," Western Digital, Jul. 2002.

International Bureau of WIPO, Search Report dated Feb. 14, 2005 for counterpart PCT Application No. PCT/US2004/029842.

\* cited by examiner

ROTARY BLOOD PUMP WITH OPPOSING SPINDLE MAGNETS, BORE AND DRIVE WINDINGS

CROSS-REFERENCE TO RELATED APPLICATIONS

This application is a divisional of U.S. patent application Ser. No. 10/940,419 filed Sep. 14, 2004, now U.S. Pat. No. 7,431,688 which claims the benefit of U.S. Provisional Application No. 60/504,233 of Wampler et al. filed Sep. 18, 2003, both of which are incorporated herein by reference.

FIELD OF THE INVENTION

This invention relates to the field of rotary pumps. In particular, this invention is drawn to bearings for various rotor and impeller architectures.

BACKGROUND OF THE INVENTION

Typical rotary pumps utilize an impeller wherein the movement of the impeller is constrained in five degrees of freedom (two angular, three translational) by mechanical contact bearings. Some working fluids may be damaged by the mechanical contact bearings. Blood pumped through pumps with contact bearings can experience hemolysis, i.e., damage to blood cells. In general, a hydraulically efficient and power efficient pump that can handle delicate working fluids such as blood is desirable for some applications.

U.S. Pat. No. 6,234,772 B1 of Wampler, et al., ("Wampler") describes a centrifugal blood pump having a repulsive radial magnetic bearing and an axial hydrodynamic bearing. U.S. Pat. No. 6,250,880 B1 of Woodard, et al. ("Woodard") describes a centrifugal blood pump with an impeller supported exclusively by hydrodynamic forces.

Both blood pumps are based on an axial flux gap motor design. The pump impeller carries the motor drive magnets thus serving as a motor rotor. In both cases, the drive magnets are disposed within the blades of the impeller. Drive windings reside outside the pump chamber but within the pump housing that serves as the motor stator. Integration of the motor and pump enables the elimination of drive shafts and seals for the pumps. The pump/motors include a back iron to increase the magnetic flux for driving the impeller.

Both blood pumps suffer from hydraulic inefficiencies due at least in part to the large, unconventional blade geometry required for disposing the magnets within the impeller blades.

The natural attraction between the magnets carried by the impeller and the back iron creates significant axial forces that must be overcome in order for the pump to work efficiently. Hydrodynamic bearings can damage blood cells as a result of shear forces related to the load carried by the hydrodynamic bearings despite the lack of contact between the impeller and the pump housing. Thus exclusive reliance on hydrodynamic bearings may be harmful to the blood.

SUMMARY OF THE INVENTION

In view of limitations of known systems and methods, various "contactless" bearing mechanisms are provided for a rotary pump as alternatives to mechanical contact bearings. Various rotor and housing design features are provided to achieve magnetic or hydrodynamic bearings. These design features may be combined. The lack of mechanical contact bearings enables longer life pump operation and less damage to working fluids such as blood.

In one embodiment, the pump includes a magnetic thrust bearing. The pump includes a pump housing defining a pumping chamber. The pump housing has a spindle extending into the pumping chamber. A spindle magnet assembly comprising first and second magnets is disposed within the spindle. The first and second magnets of the spindle magnet assembly are arranged proximate each other with their respective magnetic vectors opposing each other. The pump includes a rotor having an impeller configured to rotate about the spindle. A rotor magnet assembly comprising first and second magnets is disposed within a non-bladed portion of the rotor. The first and second magnets of the rotor magnet assembly are arranged proximate each other with their respective magnetic vectors opposing each other. The relative orientations of the spindle and rotor magnet assemblies are selected so that the spindle and rotor magnet assemblies attract each other. The rotor may include a grooved bore. In various embodiments, a hydrodynamic bearing is included for radial or axial support or both.

BRIEF DESCRIPTION OF THE DRAWINGS

The present invention is illustrated by way of example and not limitation in the figures of the accompanying drawings, in which like references indicate similar elements and in which.

DETAILED DESCRIPTION

Figure 1:
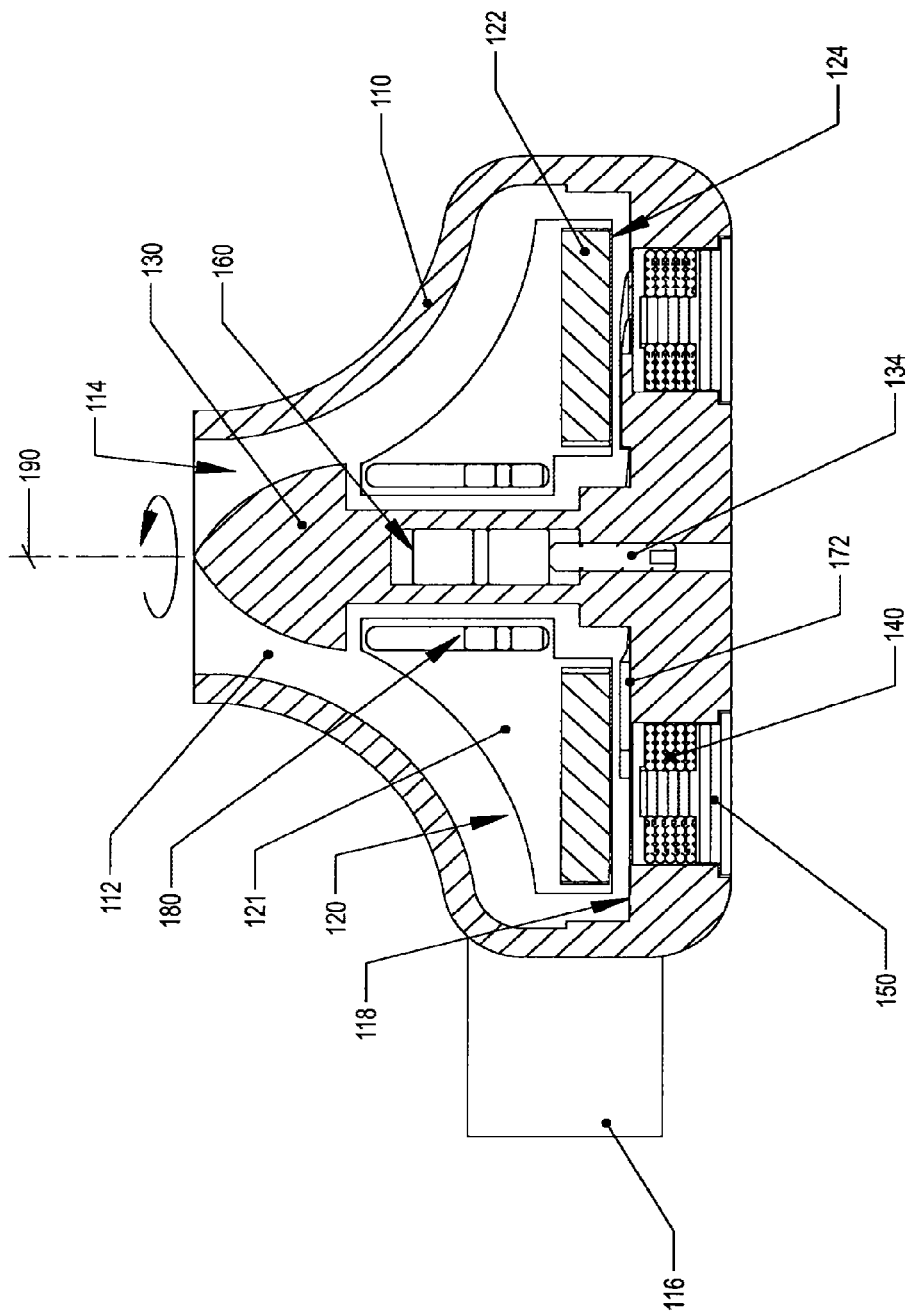
FIG. 1 illustrates a cross-section of a pump having a passive magnetic axial bearing.

FIG. 1 illustrates one embodiment of a centrifugal blood pump. The pump comprises a housing 110 defining a pumping chamber 112 between an inlet 114 and an outlet 116. Within the pumping chamber, a rotor 120 rotates about a spindle 130 protruding from a base of the pump housing. The rotor further comprises a bladed portion defining an impeller that provides the fluid moving surfaces. The impeller comprises one or more blades 121 that move fluids when the impeller rotates.

The terms "rotor" and "impeller" may be used interchangeably in some contexts. For example, when the rotor is rotating, the blade portion of the rotor is inherently rotating such that reference to rotation of either the impeller or the rotor is sufficient to describe both. When necessary, however, the term "non-bladed portion of the rotor" or "rotor excluding the impeller" may be used to specifically identify portions of the rotor other than the blades. Each blade of the rotor may separately be referred to as an impeller, however the term "impeller" is generally used to refer to a collective set of one or more blades.

The pump is based upon a moving magnet axial flux gap motor architecture. In one embodiment, the motor is a brushless DC motor. Drive magnets 122 carried by the rotor have magnetic vectors parallel to the rotor axis of rotation 190. In the illustrated embodiment, the drive magnets are disposed within a non-bladed portion of the rotor.

Drive windings 140 are located within the pump housing. Power is applied to the drive windings to generate the appropriate time-varying currents that interact with the drive magnets in order to cause the impeller to rotate. A back iron 150 enhances the magnetic flux produced by the motor rotor magnets. In one embodiment, either the face 124 of the bottom of the rotor or the opposing face 118 provided by the lower pump housing have surfaces (e.g., 172) contoured to produce a hydrodynamic bearing when the clearance between the rotor and the housing falls below a pre-determined threshold. In one embodiment, the pre-determined threshold is within a range of 0.0002 inches to 0.003 inches.

The natural attraction between the back iron 150 and the drive magnets 122 carried by the rotor can create a significant axial load on the rotor. This axial load is present in centrifugal pumps based on an axial flux gap motor architecture such as Wampler or Woodard. Woodard and Wampler both rely on hydrodynamic thrust bearings to overcome this axial loading force. Despite the lack of contact, hydrodynamic bearings can still damage blood cells as a result of shear forces related to the load carried by the hydrodynamic bearings.

The repulsive radial magnetic bearing of Wampler exacerbates the axial loads created by the magnetic attraction between the drive magnets and the back iron. Although the repulsive radial magnetic bearing creates radial stability, it introduces considerable axial instability. This axial instability can contribute further to the axial loading. This additional axial loading creates greater shear forces for any axial hydrodynamic bearing that can cause undesirable hemolysis for blood applications. In addition, the power required to sustain the hydrodynamic bearing increases as the load increases. Thus highly loaded hydrodynamic bearings can impose a significant power penalty.

The blood pump of FIG. 1 includes a magnetic axial bearing that serves to reduce or offset the axial load imposed on the rotor by the interaction between the drive magnets and the back iron. The axial magnetic bearing is formed by the interaction between a spindle magnet assembly 160 disposed within the spindle and a rotor magnet assembly 180 carried by the rotor. In the illustrated embodiment, the rotor magnet assembly 180 is disposed proximate the impeller, but the magnets of the rotor magnet assembly are not located within the blades. A set screw 134 permits longitudinal adjustment of the axial position of the axial magnetic bearing by moving the spindle magnet assembly along a longitudinal axis of the spindle.

Figure 2:
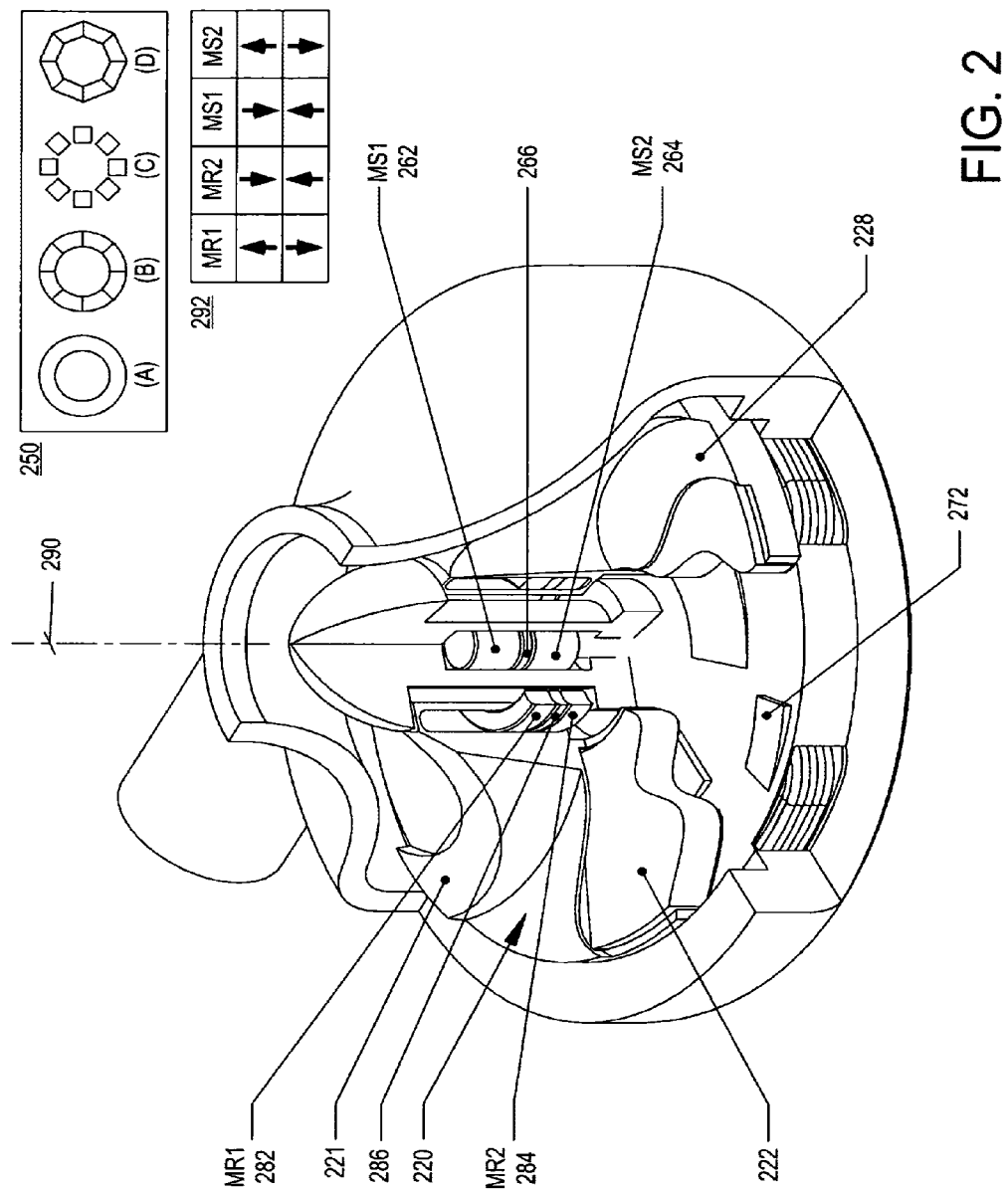
FIG. 2 illustrates one embodiment of the passive magnetic axial bearing.

FIG. 2 illustrates one embodiment of the axial magnetic bearing. The rotor magnet assembly includes a first rotor bearing magnet 282 and a second rotor bearing magnet 284 proximately disposed to each other. The first and second rotor bearing magnets are permanent magnets. In one embodiment, a pole piece 286 is disposed between them. A pole piece or flux concentrator serves to concentrate the magnetic flux produced by rotor bearing magnets 282 and 284. In an alternative embodiment, element 286 is merely a spacer to aid in positioning the first and second bearing magnets 282, 284 and does not serve to concentrate any magnetic flux. In other embodiments, element 286 is omitted so that the rotor magnet assembly does not include a spacer or a pole piece element.

In one embodiment, elements 282 and 284 are monolithic, ring-shaped permanent magnets. In alternative embodiments, the bearing magnets may be non-monolithic compositions. For example, a bearing magnet may be composed of a plurality of pie-shaped, arcuate segment-shaped, or other-shaped permanent magnet elements that collectively form a ring-shaped permanent magnet structure.

The rotor axial bearing magnet assembly is distinct from the drive magnets 222 carried by a portion of the rotor other than the blades 221. In the illustrated embodiment, the drive magnets are disposed within the non-bladed portion 228 of the rotor.

The spindle magnet assembly includes a first spindle bearing magnet 262 and a second spindle bearing magnet 264. The first and second spindle bearing magnets are permanent magnets. In one embodiment, a pole piece 266 is disposed between them. Pole piece 266 concentrates the magnetic flux produced by the spindle bearing magnets 262 and 264. In an alternative embodiment, element 266 is merely a spacer for positioning the first and second spindle bearing magnets and does not serve to concentrate any magnetic flux. In other embodiments, element 266 is omitted so that the spindle magnet assembly does not include a spacer or a pole piece element.

In the illustrated embodiment, permanent magnets 262 and 264 are cylindrical. Other shapes may be utilized in alternative embodiments. The ring-shaped rotor magnets rotate with the impeller about a longitudinal axis of the spindle that is shared by the spindle bearing magnet assembly.

The permanent magnets of each of the spindle and rotor bearing assemblies are arranged such that the magnetic vectors of the individual magnets on either side of the intervening pole pieces oppose each other. Each side of a given pole piece is adjacent the same pole of different magnets. Thus the magnetic vectors of magnets 262 and 264 oppose each other (e.g., N-to-N or S-to-S). Similarly, the magnetic vectors of magnets 282 and 284 oppose each other.

The orientation of the magnets is chosen to establish an axial attraction whenever the bearings are axially misaligned. Note that the relative orientations of the spindle and rotor magnet assemblies are selected so that the spindle and rotor magnet assemblies attract each other (e.g., S-to-N, N-to-S). The magnet vector orientation selected for the magnets of one assembly determines the magnetic vector orientation for the magnets of the other assembly. Table 292 illustrates the acceptable magnetic vector combinations for the first and second rotor bearing magnets (MR1, MR2) and the first and second spindle bearing magnets (MS1, MS2). Forces such as the magnetic attraction between the back iron and drive magnets that tend to axially displace the magnet bearing assemblies are offset at least in part by the magnetic attraction between the axial bearings that provide an axial force to restore the axial position of the rotor.

FIG. 2 also illustrates wedges or tapered surfaces 272 that form a portion of a hydrodynamic bearing when the clearance between a face of the non-bladed portion of the rotor (see, e.g., bottom face 124 of FIG. 1) and the back of the pump housing falls below a pre-determined threshold. In various embodiments, this pre-determined threshold is within a range of 0.0002 inches to 0.003 inches. Thus in one embodiment, the pump includes an axial hydrodynamic bearing. The surface geometry providing the axial hydrodynamic bearing may be located on the rotor or the housing.

Although the spindle magnet assembly is intended to provide an axial magnetic bearing, the attractive force between the spindle and rotor magnet assemblies also has a radial component. This radial component may be utilized to offset radial loading of the impeller due to the pressure gradient across the impeller. The radial component also serves as a pre-load during initial rotation and a bias during normal operation to prevent eccentric rotation of the rotor about the spindle. Such an eccentric rotation can result in fluid whirl or whip which is detrimental to the pumping action. The biasing radial component helps to maintain or restore the radial position of the rotor and the pumping action, for example, when the pump is subjected to external forces as a result of movement or impact.

Instead of a spindle magnet assembly interacting with a rotor bearing magnet assembly to form the magnetic bearing, a ferromagnetic material might be used in lieu of one of a) the spindle magnet assembly, or b) the rotor bearing magnet assembly (but not both) in alternative embodiments.

The magnetic bearing is still composed of a spindle portion and a rotor portion, however, one of the spindle and the rotor portions utilizes ferromagnetic material while the other portion utilizes permanent magnets. The ferromagnetic material interacts with the magnets to create a magnetic attraction between the rotor and spindle. Examples of ferromagnetic materials includes iron, nickel, and cobalt.

In one embodiment, the ferromagnetic material is "soft iron". Soft iron is characterized in part by a very low coercivity. Thus irrespective of its remanence or retentivity, soft iron is readily magnetized (or re-magnetized) in the presence of an external magnetic field such as those provided by the permanent magnets of the magnetic bearing system.

Figure 3:
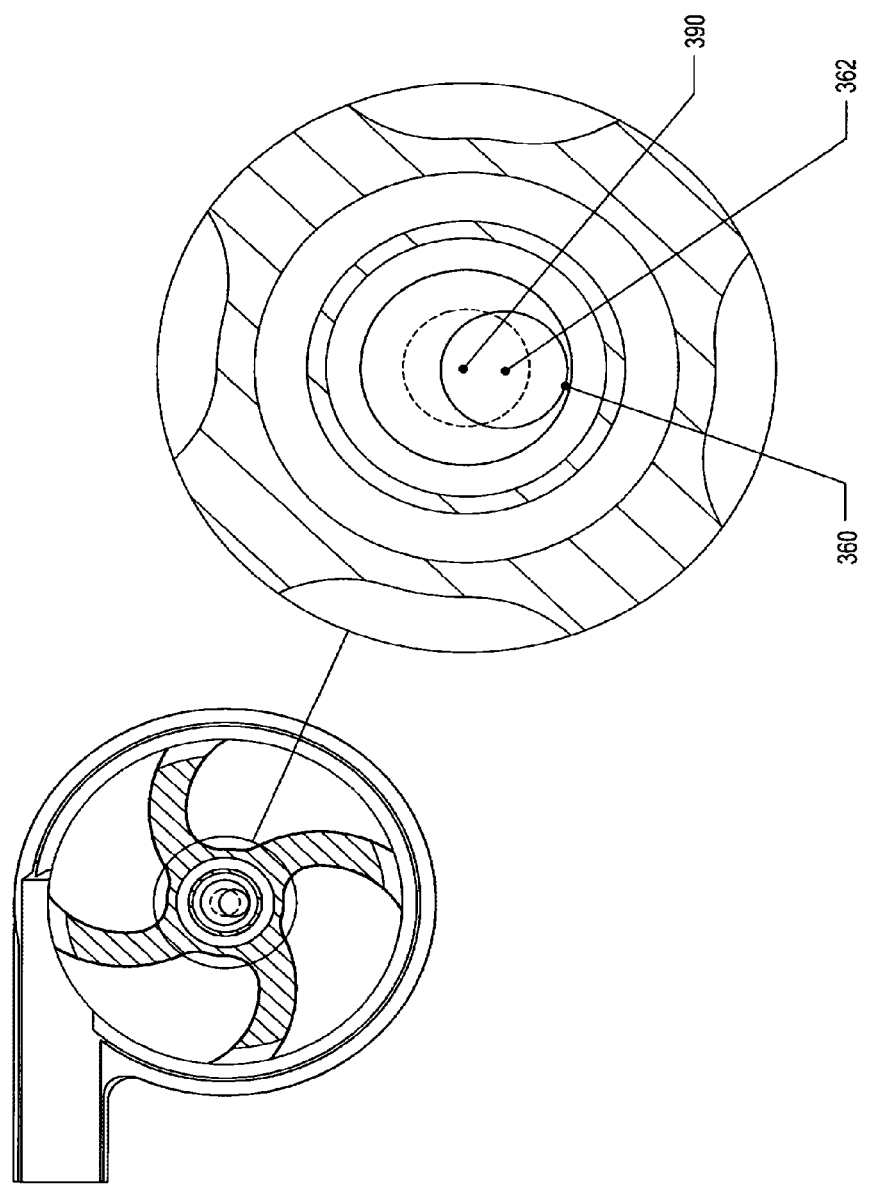
FIG. 3 illustrates center and off-center placement of the passive magnetic axial bearing.

FIG. 3 illustrates various locations for the placement of the spindle portion of the magnetic bearing. In one embodiment, the spindle magnet assembly 360 is axially aligned with a longitudinal axis 390 of the spindle so that the spindle and spindle magnet assembly share the same central longitudinal axis. In an alternative embodiment, the spindle magnet assembly is radially offset so that the spindle and spindle magnet assembly do not share the same central axis. In particular, the longitudinal axis 362 of the spindle magnet assembly 360 is displaced from the longitudinal axis 390 of the spindle. This latter positioning may be desirable to provide some radial biasing force. A difference in pressure across the impeller tends to push the impeller radially towards one side of the pump housing. This radial load may be offset at least in part by offsetting the spindle magnet assembly.

Although the spindle and rotor magnet assemblies are illustrated as comprising 2 magnetic elements each, the magnet assemblies may each comprise a single magnet instead. A greater spring rate may be achieved with multiple magnetic elements per assembly configured as illustrated instead of a single magnet per assembly. The use of two magnetic elements per assembly results in a bearing that tends to correct bi-directional axial displacements from a position of stability (i.e., displacements above and below the point of stability) with a greater spring rate than single magnetic elements per assembly.

The magnetic force generated by the axial magnetic bearing will exhibit a radial component in addition to their axial components. The radial component will tend to de-stabilize the impeller. In particular, the radial component may introduce radial position instability for the magnetic bearing of either FIG. 1 or 2.

This radial instability may be overcome using radial hydrodynamic bearings. Referring to FIG. 1, the pump may be designed for a radial hydrodynamic bearing (i.e., hydrodynamic journal bearing) located between the spindle 130 and the rotor along the bore of the rotor. The clearances illustrated in FIG. 1 are exaggerated. Hydrodynamic journal bearings require narrow clearances to be effective. In various embodiments, the hydrodynamic journal bearing clearances range from 0.0005-0.020 inches. The surface geometries suitable for axial (thrust) or radial (journal) hydrodynamic bearings may be located on either the rotor or on an associated portion of the housing (or spindle). In one embodiment, the surface geometry includes features such as one or more pads (i.e., a feature creating an abrupt change in clearance such as a step of uniform height). In alternative embodiments, the surface geometry includes features such as one or more tapers.

Figure 4:
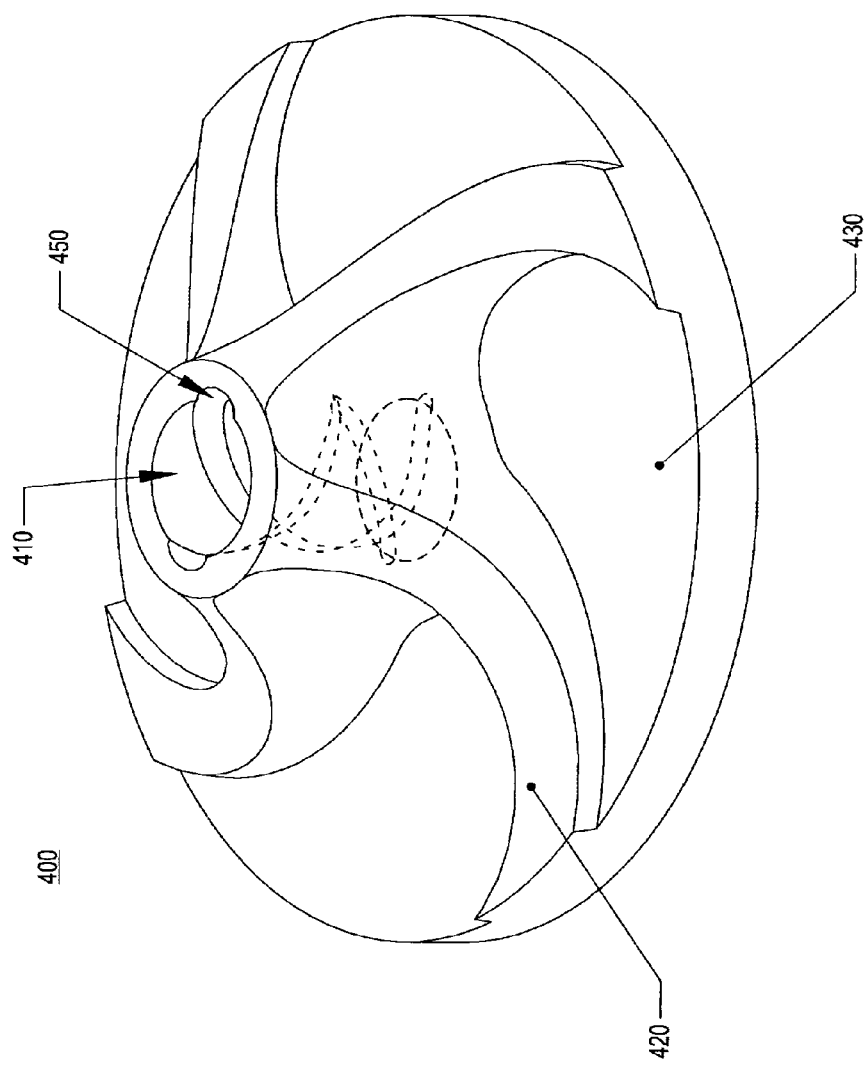
FIG. 4 illustrates one embodiment of an impeller.

FIG. 4 illustrates one embodiment of the rotor 400 including an impeller. The impeller includes a plurality of blades 420 used for pumping the working fluid such as blood. The rotor includes a bore 410. The rotor bore is coaxially aligned with the longitudinal axis of the spindle within the pump housing. Drive magnets (not illustrated) are disposed within the non-bladed portion 430 of the rotor (i.e., within the rotor but not within any blades of the impeller portion of the rotor). The motor rotor and pump impeller are thus integrated so that a drive shaft is not required. Elimination of the drive shaft also permits elimination of shaft seals for the pump.

In one embodiment, the rotor has a grooved bore. In particular, the bore has one or more helical grooves 450. The bore grooves have a non-zero axial pitch. The groove is in fluid communication with the working fluid of the pump during operation of the pump.

Figure 5:
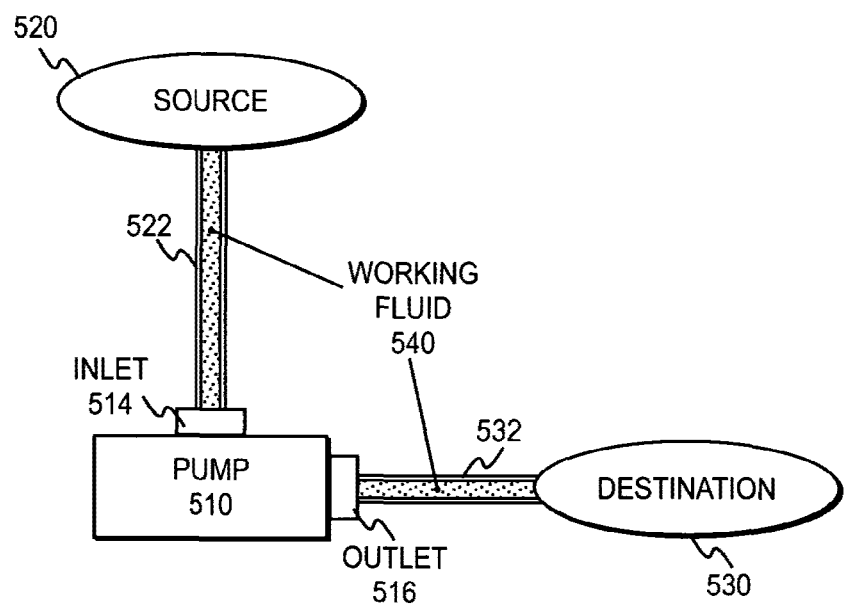
FIG. 5 illustrates one embodiment of the pump applied in a medical application.

FIG. 5 illustrates the pump 510 operationally coupled to move a working fluid 540 from a source 520 to a destination 530. A first working fluid conduit 522 couples the source to the pump inlet 514. A second working fluid conduit 532 couples the pump outlet 516 to the destination. The working fluid is the fluid moved by the pump from the source to the destination. In a medical application, for example, the working fluid might be blood. In one embodiment, the source and destination are arteries such that the pump moves blood from one artery to another artery.

Various "contactless" bearing mechanisms have been described as alternatives to mechanical contact bearings for rotary pumps. In particular, rotor, impeller, and housing design features are provided to achieve hydrodynamic or magnetic bearings. These design features may be used in conjunction with each other, if desired.

In the preceding detailed description, the invention is described with reference to specific exemplary embodiments thereof. Various modifications and changes may be made thereto without departing from the broader spirit and scope of the invention as set forth in the claims. The specification and drawings are, accordingly, to be regarded in an illustrative rather than a restrictive sense.

The invention claimed is:

1. A centrifugal pump apparatus for pumping a liquid comprising:
    a housing;
    a rotor having a bore, the rotor comprising an impeller having at least one blade; and a rotor magnet assembly comprising a first and a second magnet disposed within the rotor, wherein the first and second magnets are arranged proximate each other with their respective magnetic vectors being substantially parallel to an axis of said rotor;
    a spindle associated with said rotor, said spindle having a spindle magnet assembly comprising a third and a fourth magnet disposed within the spindle, wherein the third and fourth magnets are arranged proximate each other with their respective magnetic vectors being substantially parallel with an axis of said spindle, and
    said rotor magnet assembly and said spindle magnet assembly constituting a passive axial magnetic bearing wherein a relative orientation of the spindle and rotor magnet assemblies are selected so that the spindle and rotor magnet assemblies attract each other;
    a surface geometry including a plurality of features that create a change in clearance between said rotor and said housing and thereby create at least one hydrodynamic bearing; and,
    at least one drive magnet carried by said rotor, said at least one drive magnet having a magnetic vector substantially parallel to said axis of said rotor;

wherein said passive axial magnetic bearing and said at least one hydrodynamic bearing constitute the sole bearings for levitating said rotor during rotation of said rotor.

2. The apparatus of claim 1 wherein the rotor magnet assembly further comprises a pole piece disposed between the first and second magnets.

3. The apparatus of claim 1 wherein at least one of the first and second rotor magnets has a ring shaped form factor.

4. The apparatus of claim 1 wherein the first and second rotor magnets are concentrically located about a longitudinal axis of the rotor bore.

5. The apparatus of claim 1 wherein said features are disposed on said rotor.

6. The apparatus of claim 1 wherein said features are disposed on said housing.

7. The apparatus of claim 1 wherein said features are comprised of pads disposed on said housing.

8. The apparatus of claim 1, wherein said features are comprised of tapers disposed on said housing.

9. A centrifugal pump apparatus for pumping a liquid comprising:
- a pump housing defining a pumping chamber, the pump housing having a spindle extending into the pumping chamber;
- a rotor configured to rotate about the spindle, the rotor including an impeller comprising at least one blade;
- a rotor portion of a magnetic bearing disposed within a non-bladed portion of the rotor;
- a spindle portion of the magnetic bearing disposed within the spindle,
- said rotor portion and said spindle portion of said magnetic bearing constituting a passive axial magnetic bearing
- wherein the spindle and rotor portions of the magnetic bearing are configured to attract each other,
- wherein at least one of the rotor and spindle portions of the magnetic bearing comprises a first and a second magnet,
- wherein the first and second magnets are arranged proximate each other with their respective magnetic vectors being substantially parallel to an axis of said at least one of said rotor and spindle; and,
- at least one drive magnet carried by said rotor, said at least one drive magnet having a magnetic vector substantially parallel to said axis of said rotor;
- a surface geometry including a plurality of features that create a change in the clearance between said rotor and said housing and thereby create at least one hydrodynamic bearing; and,
- wherein said passive axial magnetic bearing and said at least one hydrodynamic bearing constitute the sole bearings for levitating said rotor during rotation of said rotor.

10. The apparatus of claim 9 wherein the spindle portion of the magnetic bearing comprises first and second magnets arranged proximate each other with their respective magnetic vectors opposing each other, wherein the rotor portion of the magnetic bearing comprises first and second magnets arranged proximate each other with their respective magnetic vectors opposing each other.

11. The apparatus of claim 9 wherein the spindle portion of the magnetic bearing comprises first and second magnets arranged proximate each other with their respective magnetic vectors opposing each other, wherein the rotor portion of the magnetic bearing comprises ferromagnetic material.

12. The apparatus of claim 11 wherein the ferromagnetic material is soft iron.

13. The apparatus of claim 9 wherein the rotor portion of the magnetic bearing comprises first and second magnets arranged proximate each other with their respective magnetic vectors opposing each other, wherein the spindle portion of the magnetic bearing comprises ferromagnetic material.

14. The apparatus of claim 13 wherein the ferromagnetic material is soft iron.

* * * * *